(12) United States Patent
Pretz et al.

(10) Patent No.: US 10,647,634 B2
(45) Date of Patent: May 12, 2020

(54) PROCESS FOR CATALYTIC DEHYDROGENATION

(71) Applicant: Dow Global Technologies LLC, Midland, MI (US)

(72) Inventors: Matthew T. Pretz, Freeport, TX (US); Lin Luo, Freeport, TX (US)

(73) Assignee: Dow Global Technologies LLC, Midland, MI (US)

( * ) Notice: Subject to any disclaimer, the term of this patent is extended or adjusted under 35 U.S.C. 154(b) by 0 days.

(21) Appl. No.: 16/097,719

(22) PCT Filed: May 3, 2017

(86) PCT No.: PCT/US2017/030782
§ 371 (c)(1),
(2) Date: Oct. 30, 2018

(87) PCT Pub. No.: WO2017/196602
PCT Pub. Date: Nov. 16, 2017

(65) Prior Publication Data
US 2019/0161422 A1    May 30, 2019

Related U.S. Application Data

(60) Provisional application No. 62/333,313, filed on May 9, 2016.

(51) Int. Cl.
C07C 5/333    (2006.01)
(52) U.S. Cl.
CPC ........... *C07C 5/3337* (2013.01); *Y02P 20/584* (2015.11)

(58) Field of Classification Search
CPC ................ C07C 2523/62; C07C 11/06; C07C 5/32–3337; Y02P 20/584; B01J 23/62
See application file for complete search history.

(56) References Cited

U.S. PATENT DOCUMENTS 2,280,072 A * 4/1942 Wood et al. ............ C09B 47/08
540/140
2,889,383 A * 6/1959 Green ................... C07C 5/3332
585/602

(Continued)

FOREIGN PATENT DOCUMENTS

EP    0637578 A1    2/1995
WO    02096844 A1    12/2002

(Continued)

OTHER PUBLICATIONS

Geldart, D., Characterization of Fluidized Powders, Gas Fluidization Technology, 1986, 38-48.

(Continued)

*Primary Examiner* — Ali Z Fadhel
(74) *Attorney, Agent, or Firm* — Dinsmore & Shohl LLP

(57) ABSTRACT

A process for catalytic dehydrogenation comprising mixing fluidization gas a fluidization gas which comprises methane, natural gas, ethane, hydrogen, nitrogen or any combination thereof with a fluidized catalyst stream that has passed through a catalytic dehydrogenation reactor and has exited a catalyst separation zone to form a catalyst recycle stream; and recycling the catalyst recycle stream either directly or indirectly into a catalytic dehydrogenation reactor is provided.

18 Claims, 7 Drawing Sheets

(56) References Cited

U.S. PATENT DOCUMENTS

| | | | |
|---|---|---|---|
| 4,615,792 A * | 10/1986 | Greenwood | B01J 8/12 |
| | | | 208/134 |
| 6,031,143 A | 2/2000 | Buonomo et al. | |
| 2004/0242945 A1 | 12/2004 | Pelati et al. | |
| 2008/0194891 A1* | 8/2008 | Pretz | C07C 5/3332 |
| | | | 585/252 |
| 2010/0236985 A1* | 9/2010 | Luo | B01J 23/62 |
| | | | 208/138 |

FOREIGN PATENT DOCUMENTS

| | | |
|---|---|---|
| WO | 03053567 A2 | 7/2003 |
| WO | 2005077867 A2 | 8/2005 |

OTHER PUBLICATIONS

Geldart, D., "Types of Gas Fluidization", Powder Technology, 1973, 7, 285-292.

International Search Report and Written Opinion pertaining to PCT/US2017/030782 dated Jul. 26, 2017.

Examination Report pertaining to corresponding G.C.C. Patent Application No. 2017-33314, dated Apr. 2, 2019.

* cited by examiner

PROCESS FOR CATALYTIC DEHYDROGENATION

CROSS REFERENCE TO RELATED APPLICATIONS

This application claims priority to U.S. Provisional Application No. 62/333,313, filed May 9, 2016, which is incorporated by reference in its entirety.

FIELD OF INVENTION

The disclosure relates to a process for catalytic dehydrogenation.

BACKGROUND OF THE INVENTION

A number of lower olefins and di-olefins are known to be widely used in a variety of chemical processes, both as starting materials and as intermediates. These may include, in non-limiting example, ethylene, propylene, butene, isobutene, and butadiene. While olefins and di-olefins may be by-products of some industrial processes, such as fluid catalytic cracking, the increasing need for olefins motivates development of "on-purpose" olefin and/or di-olefin production. One such "on-purpose" method is catalytic dehydrogenation of paraffins and/or other dehydrogenatable hydrocarbons.

In processes for the catalytic dehydrogenation, catalyst which has passed through the catalytic dehydrogenation reactor once or several times may still contain significant levels of activity. Such used catalyst which maintains some activity is referred to as used catalyst. Catalyst which maintains little or no activity is referred to as spent catalyst. Dehydrogenation catalysts are typically separated from a product stream after exiting the catalytic dehydrogenation reactor. Following such separation, all or part of the catalyst particles may be sent to regeneration. As some separated catalyst particles are used and maintain some activity, an economic benefit can result from recycling some of the separated catalyst. Moreover, dehydrogenation catalyst recycle may enable the catalyst feed temperature and the reactor space velocity to be controlled. It is beneficial to control the catalyst temperature in the reactor as too high temperatures results in poor selectivity. In addition, the reactor space velocity can be adjusted by way of a catalyst recycle stream thereby allowing process controllers to respond to a deactivating catalyst or potential miscalculations in the scale up.

In conventional fluid catalytic cracking systems, steam is used as a strip gas to remove any hydrocarbons entrained with the recycle catalyst. Steam is desirable in the catalytic dehydrogenation of paraffins because it will condense and easily be separated from hydrocarbons by forming a separate and distinct phase. However, steam severely deactivates the catalyst at relevant temperatures, as can be seen in FIG. 9, which illustrates an activity drop from 45% to 18%.

This disclosure addresses these issues by providing a process for recycling used dehydrogenation catalyst while maintaining catalyst activity and selectivity.

SUMMARY OF THE INVENTION

In one embodiment, the disclosure provides a process for catalytic dehydrogenation comprising mixing a fluidization gas a fluidization gas which comprises methane, natural gas, ethane, hydrogen, nitrogen or any combination thereof with a fluidized catalyst stream that has passed through a catalytic dehydrogenation reactor and has exited a catalyst separation zone to form a catalyst recycle stream; and recycling the catalyst recycle stream either directly or indirectly into a catalytic dehydrogenation reactor.

DETAILED DESCRIPTION OF THE INVENTION

The disclosure provides a process for catalytic dehydrogenation comprising mixing a fluidization gas a fluidization gas which comprises methane, natural gas, ethane, hydrogen, nitrogen or any combination thereof with a fluidized catalyst stream that has passed through a catalytic dehydrogenation reactor and has exited a catalyst separation zone to form a catalyst recycle stream; and recycling the catalyst recycle stream either directly or indirectly into a catalytic dehydrogenation reactor. The fluidization gas used in embodiments of the process disclosed herein a fluidization gas which comprises methane, natural gas, ethane, hydrogen, nitrogen or any combination thereof.

The inventive process may be used in conjunction with any catalytic dehydrogenation on-purpose process to produce olefins and/or di-olefins. U.S. Patent Application 62/139,938, PCT published application WO 2005/077867, and PCT/US16/2112, the disclosures of which are incorporated herein in their entirety, describe certain such production processes. The feedstock for such catalytic dehydrogenation processes include saturated or partially saturated hydrocarbons ("hydrocarbon feed"). Hydrocarbon feed may include one or more of:1) a paraffinic hydrocarbon compounds, preferably a lower alkane having from 2 to 6 carbon atoms but more preferably less than 5 carbon atoms, for example ethane, propane, isobutane and n-butane, to the corresponding olefin, namely, ethylene, propylene, isobutylene and n-butylene, respectively, and 2) an alkylaromatic hydrocarbon compound, preferably a lower alkylaromatic hydrocarbon compound, such as for example, ethylbenzene, propylbenzene, isopropyl benzene, and methyl ethylbenzene, to the corresponding vinyl aromatic hydrocarbon compound, (that is "alkenylaromatic"), namely, styrene, cumene or alpha-methyl styrene. Several embodiments of the present invention are described including both the simultaneous and separate dehydrogenation of lower alkanes and alkylaromatics. The invention is useful to prepare styrene and ethylene from ethylbenzene and ethane, respectively. Likewise, cumene and propylene can be prepared from propylbenzene and propane, respectively. One of ordinary skill in the art would readily recognize other potential hydrocarbon feed materials.

Figure 1:
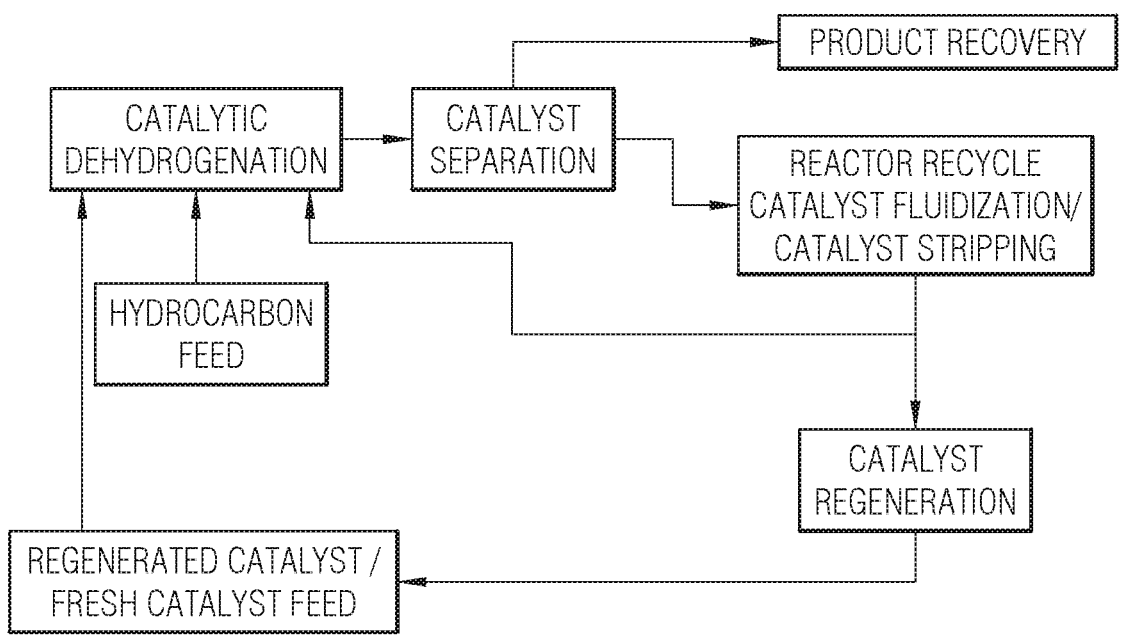
FIG. 1 is a flow diagram illustrating a first embodiment of the inventive process wherein the stripping zone of the catalyst separation section is also a reactor recycle catalyst fluidization zone.
Figure 2:
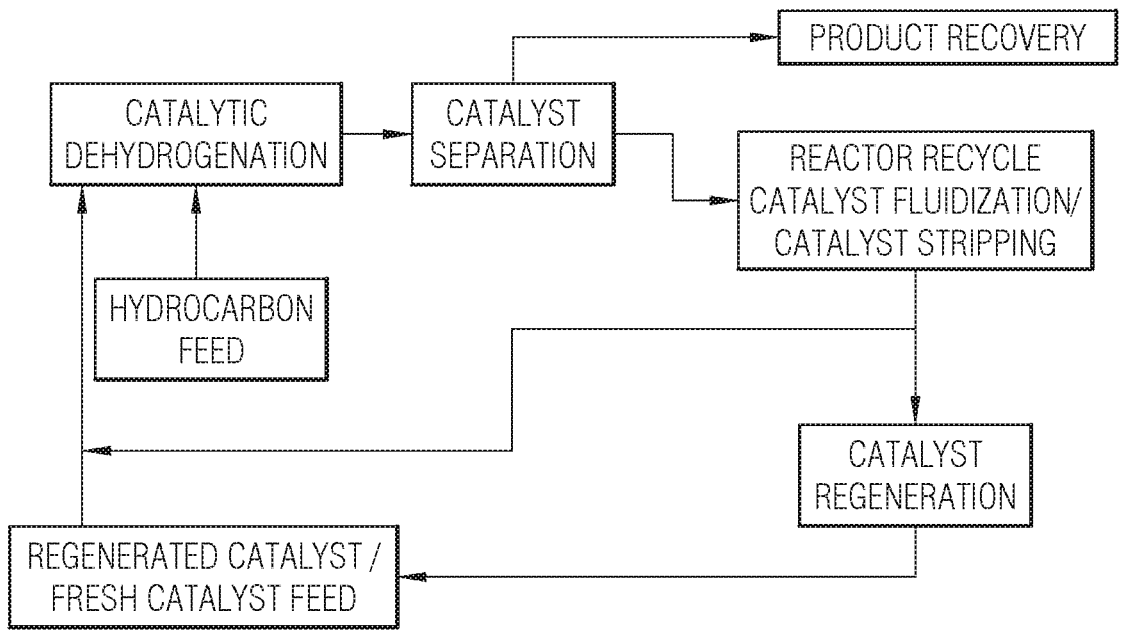
FIG. 2 is a flow diagram illustrating a second embodiment of the inventive process wherein the stripping zone of the catalyst separation section is also a reactor recycle catalyst fluidization zone.

FIGS. 1 and 2 are flow diagrams illustrating two primary methodologies for operating embodiments of the present invention. FIG. 1 illustrates catalytic dehydrogenation of a hydrocarbon in the presence of a dehydrogenation catalyst. A resulting fluidized dehydrogenation product and used catalyst stream is subjected to a catalyst separation process from which an olefinic product stream is extracted and sent to product recovery. Separated fluidized used catalyst particles are then subjected to a combined stripping and reactor recycle catalyst fluidization step. As shown in both FIGS. 1 and 2, some portion of the separated fluidized catalyst used particles will be passed into a catalyst regeneration process. Following the reactor recycle catalyst fluidization step, the fluidized used catalyst stream is passed back to the catalytic dehydrogenation step. FIG. 2 illustrates a substantially similar process except that subsequent to the combined catalyst stripping and reactor recycle catalyst fluidization step, the fluidized used catalyst stream is then sent to a mixing step in which it is mixed with regenerated and/or fresh dehydrogenation catalyst. Following such mixing step, the fluidized used catalyst along with one or both of regenerated and fresh catalyst are sent to the catalytic dehydrogenation step.

Figure 3:
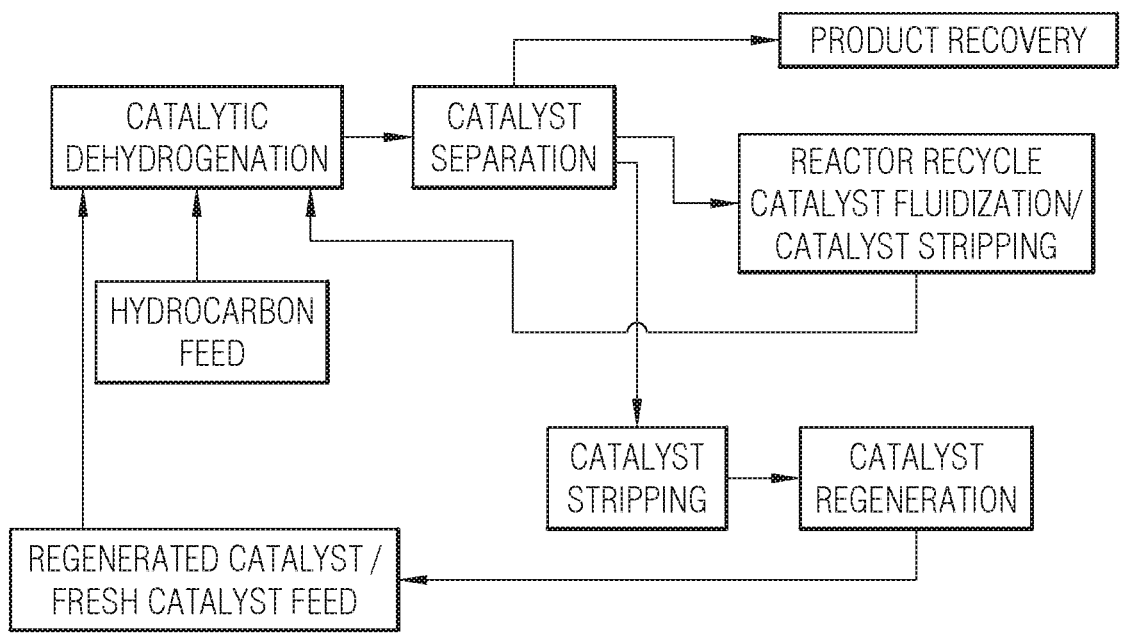
FIG. 3 is a flow diagram illustrating the first embodiment of the inventive process as shown in FIG. 1 except that the stripping zone of the catalyst separation section is separate from the reactor recycle catalyst fluidization zone.
Figure 4:
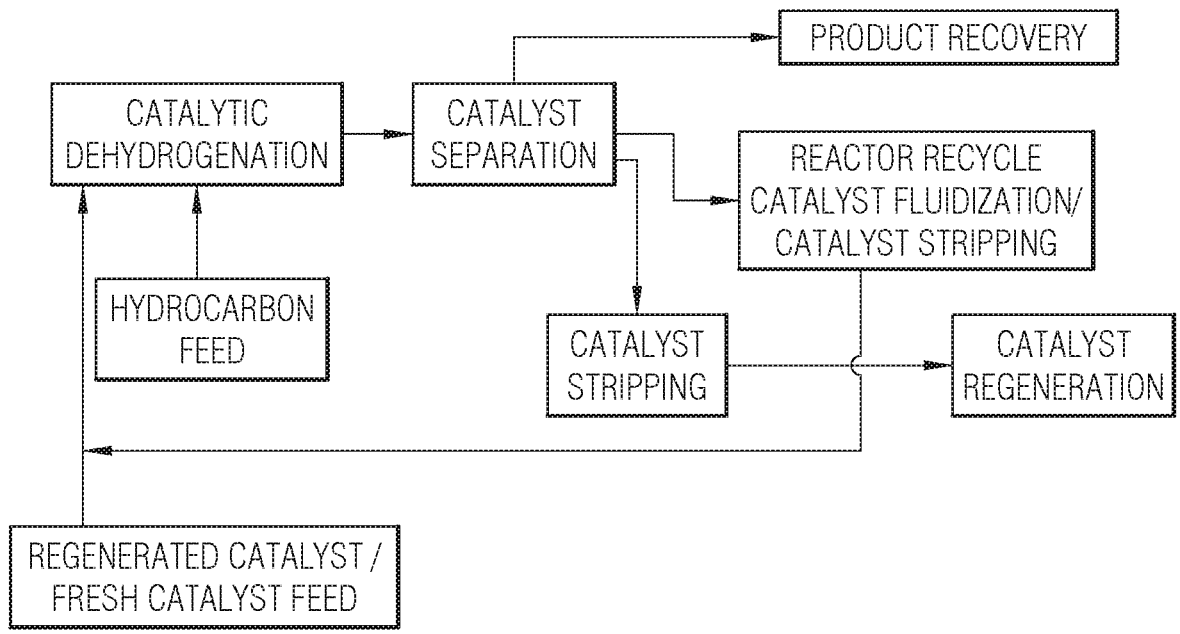
FIG. 4 is a flow diagram illustrating the second embodiment of the inventive process as shown in FIG. 2 except that the stripping zone of the catalyst separation section is separate from the reactor recycle catalyst fluidization zone.

FIGS. 3 and 4 further illustrate the processes illustrated in FIGS. 1 and 2, respectively, except that the reactor recycle catalyst fluidization step is conducted on only a portion of the separated fluidized catalyst particles and is conducted separate and apart from the catalyst stripping step. As shown in both FIGS. 3 and 4, the catalyst particles subjected to the reactor recycle catalyst fluidization step are sent directly to the catalytic dehydrogenation step (FIG. 3) or to a mixing zone (FIG. 4).

Figure 5:
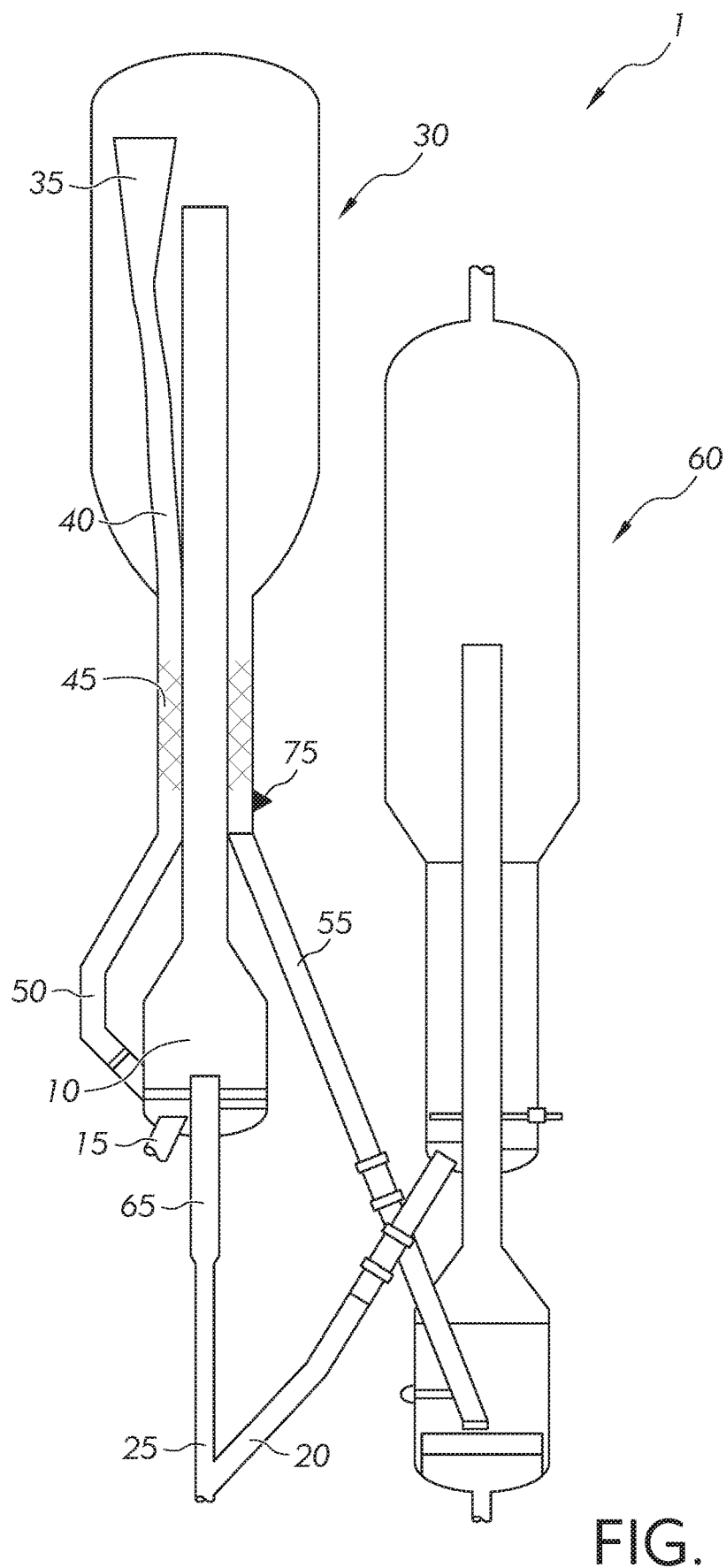
FIG. 5 is a schematic illustrating one equipment configuration for operating an embodiment of the inventive process in which the catalyst recycle stream is sent directly to the reactor.

Referring to FIG. 5 an on-purpose catalytic dehydrogenation system 1, for example, for production of propylene, is shown. Catalytic dehydrogenation system 1 includes a catalytic dehydrogenation reactor 10 into which one or more hydrocarbon feeds are injected through feed line 15. Regenerated catalyst may be fed through line 20 first into line 25 from which it is then passed into fluidized bed dehydrogenation reactor 10. A product stream exits reactor 10 passing into a catalyst separation zone 30 in which the fluidized catalyst particles are separated from the gaseous components of the product stream. In the embodiment shown in FIG. 5, the catalyst separation zone 30 comprises a plurality of cyclone separators 35, each terminating in a dipleg 40, which empties into a stripping section 45. Fluidization gas enters the reactor recycle catalyst fluidization/stripping section 45 through feed line 75 which distributes fluidization gas over the entire annular cross section in a distributor commonly used in fluidized applications. The separated catalyst particles are contacted with a gaseous mixture which comprises at least 40 vol % fluidization gas in the reactor recycle catalyst fluidization/stripping section 45. All individual values and subranges from at least 40 vol % are included and disclosed herein. For example, the gaseous component may comprises at least 40, 50, 60, 70, 80, 90, or 100 vol % fluidization gas. In a particular embodiment, the gaseous component in the reactor recycle catalyst fluidization/stripping section 45 comprises 60 vol % methane. In those embodiments in which the methane gaseous component in the stripping section 45 is less than 100 vol %, the remainder of the gaseous component may include, for example, nitrogen, hydrogen, ethane, and propane. A portion of the separated catalyst particles may enter used catalyst feed line 55 and be passed into the catalyst regenerator system 60.

In a particular embodiment, the gaseous component contains no more than 30 vol % steam. All individual values and subranges from equal to or less than 30 vol % are included and disclosed herein. For example, the gaseous component may comprise no more than 30 vol % steam, or in the alternative, no more than 20 vol % steam, or in the alternative, no more than 10 vol %.

Reactor Recycle Catalyst Fluidization Conditions

In the reactor recycle catalyst fluidization/stripping section 45, the used catalyst is contacted with a gaseous component, including at least 40 vol % fluidization gas, at a temperature from 500 to 800° C. for a period of from 1 second to 3 minutes. More preferably 10 seconds to 2 minutes, and more preferably 30 seconds to 90 seconds. All individual values and subranges from 500 to 800° C. are included and disclosed herein; for example, the temperature in the reactor recycle catalyst fluidization/stripping section 45 may range from a lower limit of 500, 575, 625, 700 or 775° C. to an upper limit of 550, 600, 650, 700, 750 or 800° C. The time and temperature of such contacting depends, at least in part, on the specific hydrocarbon feed content and the concentration and identity of fluidization gas in the gaseous component.

For example, for the catalytic dehydrogenation of ethyl benzene, the temperature in the reactor recycle catalyst fluidization/stripping section 45 may range from 560 to 620° C. All individual values and subranges from 560 to 620° C. are included and disclosed herein; for example, the reactor recycle catalyst fluidization/stripping section 45 temperature for ethylbenzene dehydrogenation may range from a lower limit of 560, 580, 590, 600 or 610° C. to an upper limit of 585, 592, 604, 616 or 620° C. For example, the reactor recycle catalyst fluidization/stripping section 45 temperature for ethylbenzene may range from 560 to 620° C., or in the alternative, from 580 to 600° C., or in the alternative, from 600 to 620° C., or in the alternative, from 585 to 615° C.

For the catalytic dehydrogenation of propane, the reactor recycle catalyst fluidization/stripping section 45 temperature may range from 580 to 640° C. All individual values and subranges from 580 to 640° C. are included and disclosed herein; for example, the reactor recycle catalyst fluidization/stripping section 45 temperature for propane catalytic dehydrogenation may range from a lower limit of 580, 600, 610, 620 or 630° C. to an upper limit of 605, 613, 622, 634 or 640° C. For example, the reactor recycle catalyst fluidization/stripping section 45 temperature for propane catalytic dehydrogenation may range from 580 to 640° C., or in the alternative, from 600 to 620° C., or in the alternative, from 620 to 640° C., or in the alternative, from 610 to 630° C.

The used catalyst is contacted with the fluidization gas in the reactor recycle catalyst fluidization/stripping section 45 for a period from 1 second to 3 minutes. All individual values and subranges from 1 second to 3 minutes are included and disclosed herein; for example the contacting period may range from a lower limit of 1, 5, 10, 30, 60, 90, 120, or 150 seconds to an upper limit of 10, 20, 50, 100, 120, 150 or 180 seconds. For example, the contacting may occur for a period of from 1 to 180 seconds, or in the alternative, from 10 to 95 seconds, or in the alternative, from 95 to 120 seconds, or in the alternative, from 20 to 120 seconds.

Figure 6:
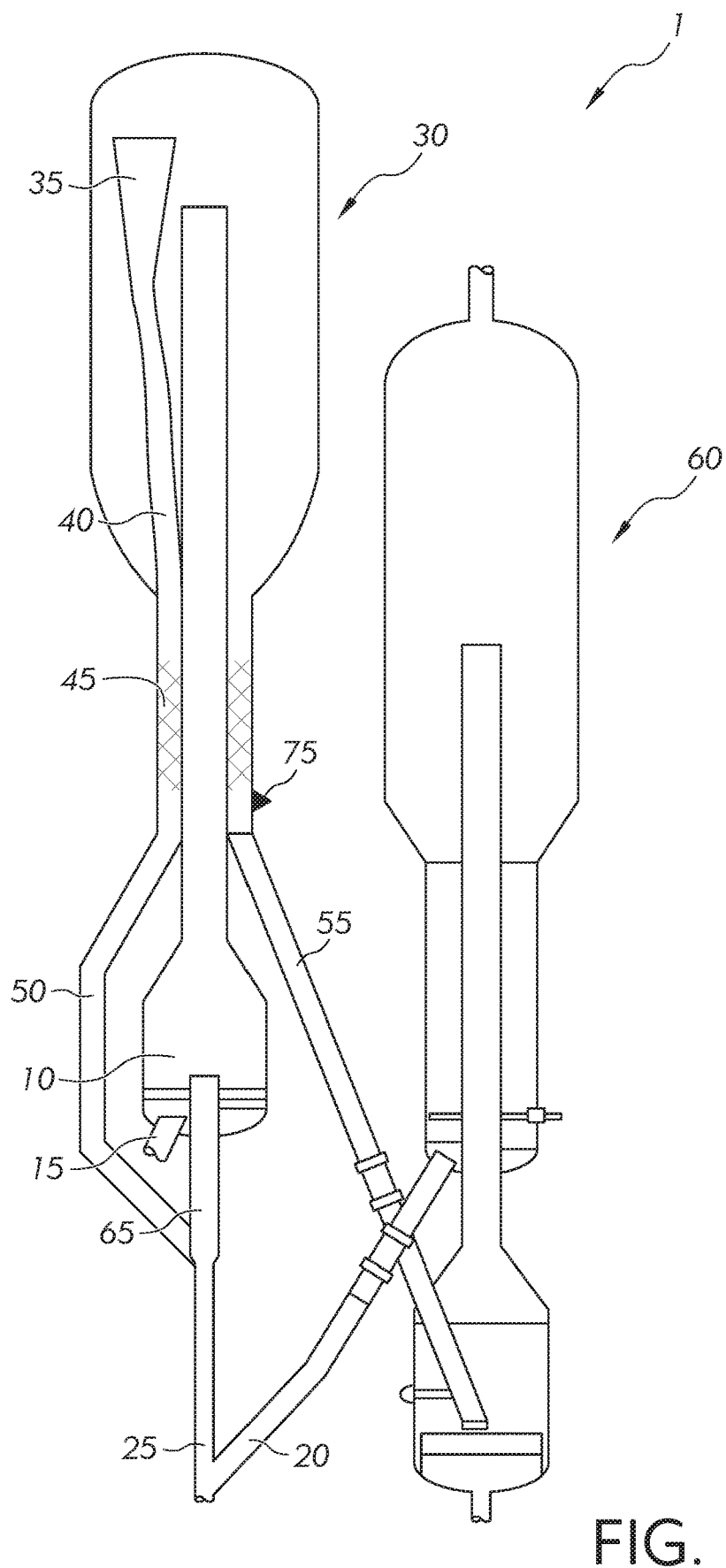
FIG. 6 is a schematic illustrating one equipment configuration for operating another embodiment of the inventive process in which the catalyst recycle stream is sent to a mixing zone prior to being sent to the reactor.

Following the contacting period in the reactor recycle catalyst fluidization/stripping section 45, the used catalyst and the gaseous component, collectively referred to as the catalyst recycle stream, are passed through line 50 into the catalytic dehydrogenation reactor 10 directly. FIG. 6 illustrates the process as shown in FIG. 5 with the exception that the catalyst recycle stream is first passed through line 57 to a mixing zone 65, in which the catalyst recycle stream may be mixed with regenerated catalyst exiting the catalyst regenerator system 60 prior to entering the dehydrogenation reactor 10.

Reactor Conditions

In those embodiments in which the catalyst recycle stream is passed directly from the reactor recycle catalyst fluidization/stripping section 45 into the catalytic dehydrogenation reactor 10, the temperature in the reactor 10 is generally from 10 to 40° C. higher than the temperature in the reactor recycle catalyst fluidization zone 50.

Mixing Zone Conditions

In those embodiments in which the catalyst recycle stream is passed into the mixing zone 65 prior to entering the catalytic dehydrogenation reactor 10, the temperature in the mixing zone 65 is generally from 10° C. to 100° C. higher than the temperature in the reactor recycle catalyst fluidization/stripping section 45.

For example, for the catalytic dehydrogenation of propane, the temperature in the mixing zone 65 may range from 640 to 680° C. All individual values and subranges from 640 to 680° C. are included and disclosed herein; for example, the temperature in the mixing zone 65 may range from a lower limit of 640, 650, 660 or 670° C. to an upper limit of 644, 655, 663, 672 or 680° C. For example, the temperature in the mixing zone 65 may range from 640 to 680° C., or in the alternative, from 640 to 660° C., or in the alternative, from 660 to 680° C., or in the alternative, from 650 to 670° C.

For example, for the catalytic dehydrogenation of ethylbenzene, the temperature in the mixing zone 65 may range from 620 to 670° C. All individual values and subranges from 620 to 670° C. are included and disclosed herein; for example, the temperature in the mixing zone 65 may range from a lower limit of 620, 630, 640, 650 or 660° C. to an upper limit of 628, 637, 646, 655, 666 or 670° C. For example, the temperature in the mixing zone 65 may range from 620 to 670° C., or in the alternative, from 620 to 645° C., or in the alternative, from 645 to 670° C., or in the alternative, from 630 to 660° C.

Additional Embodiments

Figure 7:
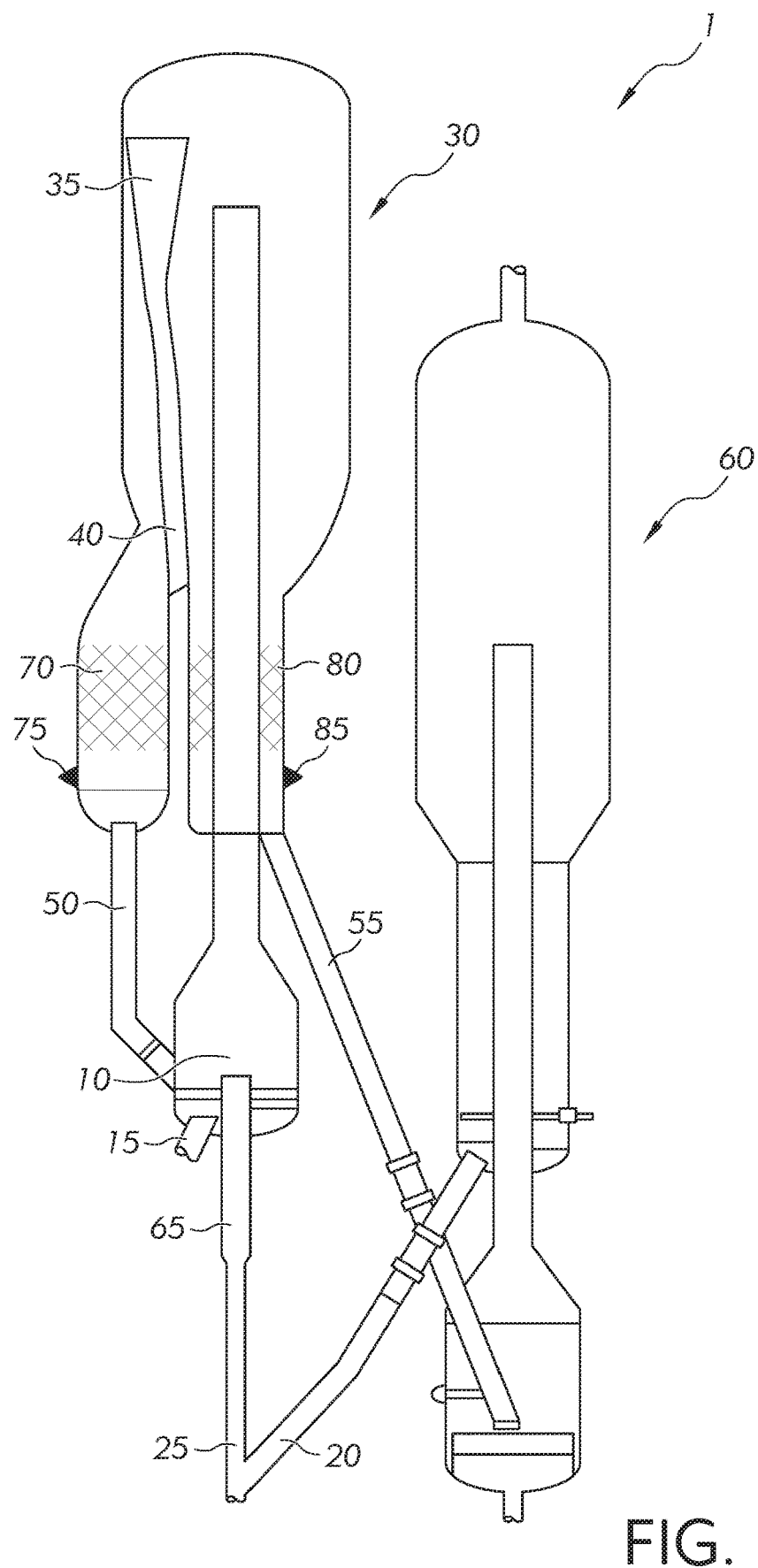
FIG. 7 is a schematic illustrating one equipment configuration for operating an embodiment of the inventive process in which the catalyst separation zone includes a side stripper used as a reactor recycle catalyst fluidization zone and the catalyst recycle stream is sent directly to the reactor.
Figure 8:
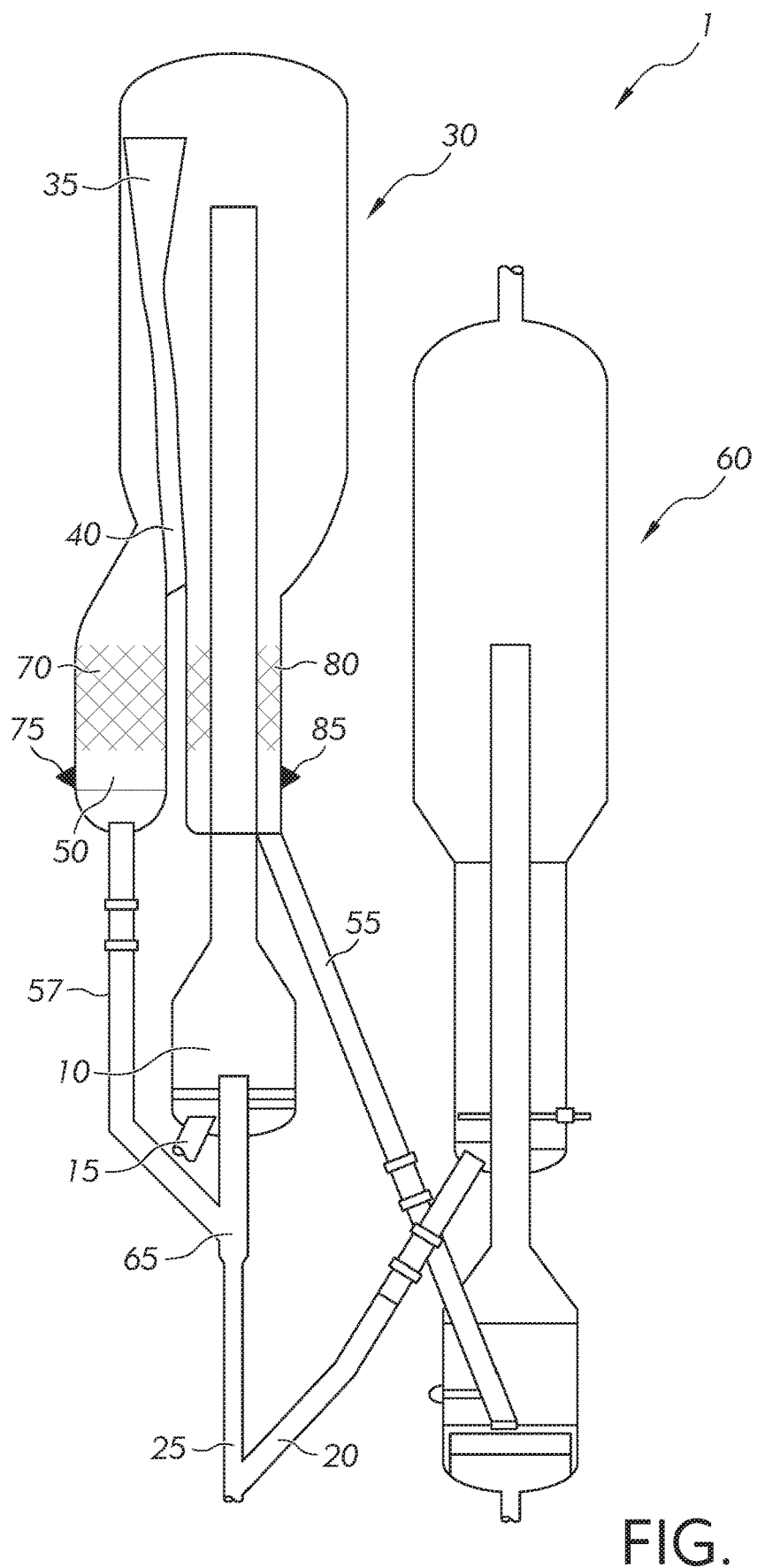
FIG. 8 is a schematic illustrating one equipment configuration for operating another embodiment of the inventive process in which the catalyst separation zone includes a side stripper used as a reactor recycle catalyst fluidization zone and the catalyst recycle stream is sent to a mixing zone prior to being sent to the reactor.
Figure 9:
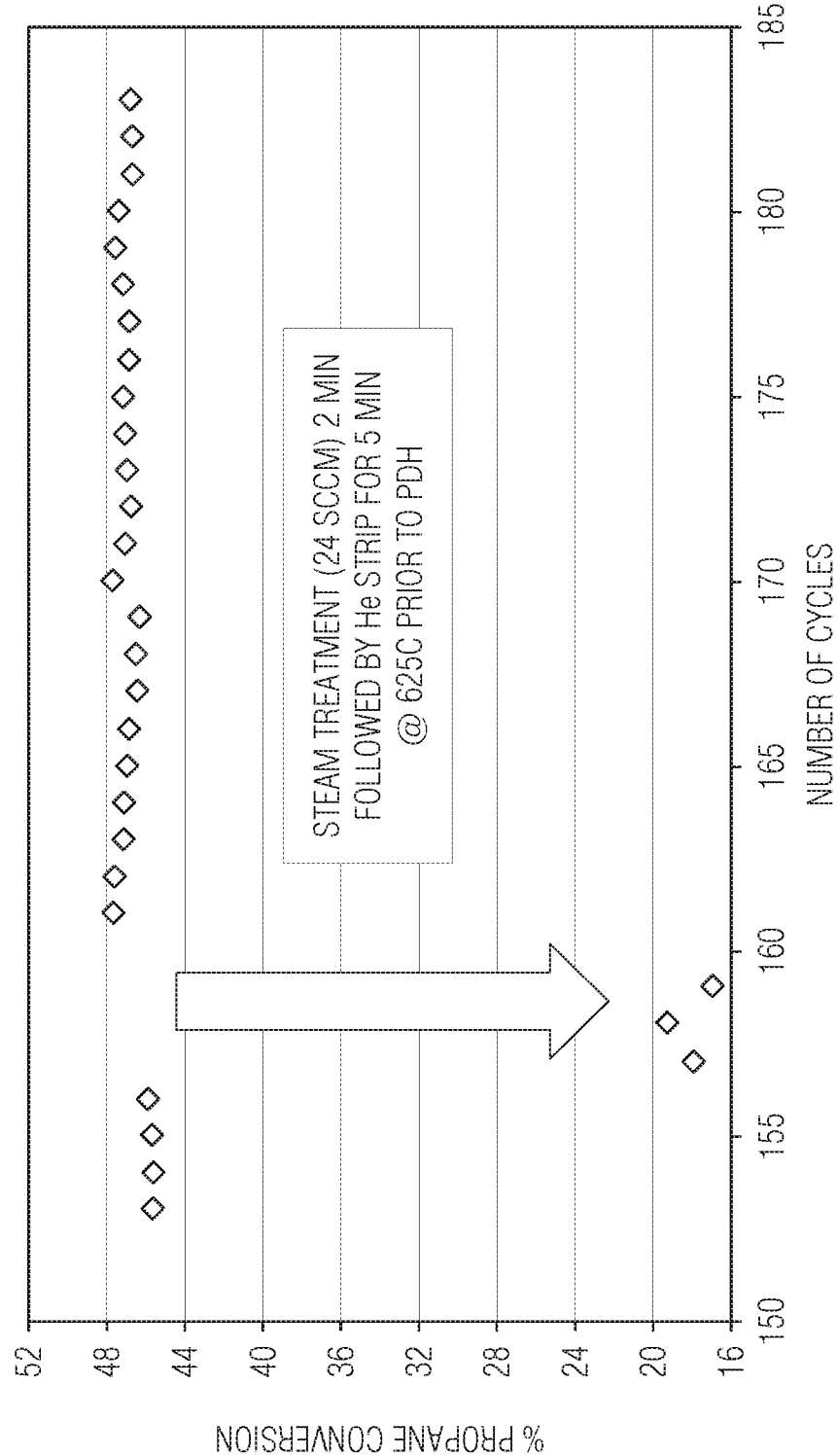
FIG. 9 is a graph depicting the deactivation of dehydrogenation catalyst by steam.

FIGS. 7 and 8 illustrate an alternative embodiment of the present invention in which the catalyst separation step terminates in two sections, the stripping section 80 and an additional reactor recycle catalyst fluidization section 70. When such reactor recycle catalyst fluidization section 70 is present, the separated used catalyst particles entering the reactor recycle catalyst fluidization section 70 are contacted with fluidization gas such as methane, natural gas, ethane, hydrogen and/or nitrogen entering through line 75. Stripping gas enters stripping section 80 by passing through line 85. Any appropriate stripping gas may be used, including for example, methane, hydrogen, steam and nitrogen. Used catalyst entering stripping section 80 is then passed into the catalyst regeneration system 60 through line 55. In FIG. 7, the fluidized used catalyst stream is sent directly to the catalytic dehydrogenation reactor 10 following exposure to fluidization gas through line 50. In FIG. 8, the fluidized used catalyst stream following exposure to fluidization gas is sent first to mixing zone 65 through line 57 prior to being passed to the catalytic dehydrogenation reactor 10. Alternatively, fluidized used catalyst stream from the reactor recycle catalyst fluidization section 70 may be sent to catalyst regenerator system 60 while the fluidized used catalyst stream from the stripping section 80 may be passed to the dehydrogenation reactor 10 or the mixing zone 65.

Embodiments of the inventive process permit the recycle of the dehydrogenation catalyst while maintaining an acceptable level of catalyst activity. For example, in the case of propane dehydrogenation, the overall conversion of propane into propylene in the catalytic dehydrogenation reactor, in the presence of recycled catalyst and regenerated catalyst, may range from 30 to 55%. All individual values and subranges from 30 to 55% are included and disclosed herein; for example, the overall propane conversion may range from a lower limit of 30, 35, 40, 45 or 50% to an upper limit of 38, 47 or 55%. For example, the overall propane conversion may range from 30 to 42%, or in the alternative, from 43 to 55%, or in the alternative, from 35 to 50%, or in the alternative, from 30 to 55%.

In another embodiment, the recycle catalyst stream following contacting with fluidization gas in the reactor recycle catalyst fluidization zone 50 has greater than 80% of the dehydrogenation activity of the fluidized catalyst stream exiting the dehydrogenation reactor. All individual values and subranges from greater than 80% are included herein and disclosed herein. For example, the recycle catalyst stream following contacting with fluidization gas has greater than 80, 82, 84, 86, or 88% of the dehydrogenation activity of the fluidized catalyst stream exiting the dehydrogenation reactor. In a particular embodiment, the recycle catalyst stream following contacting with fluidization gas has from greater than 80 to less than 100% of the dehydrogenation activity of the fluidized catalyst stream exiting the dehydrogenation reactor.

In order to access the activity of the catalyst, a sample must be withdrawn from the unit at the referenced area of the process, heated up under nitrogen in a fixed bed reactor, and the conversion of propane should be measured at a Weight Hourly Space Velocity (WHSV) (lb/hr propane/lb of catalyst in reactor) of 10 $hr^{-1}$ with a gas chromatograph at approximately the same catalyst to propane feed ratio as observed in the plant. For example, if the catalyst to propane feed ratio is the plant was 20, then the experiment should feed 20 times more mass of propane that catalyst in the experiment and then the composition of the product should be measured.

The catalytic selectivity of the propane catalytically reacted is expected to be greater than 95 carbon mol % to propylene. Alternatively, the thermal reaction of propane is suspected to provide about a 45 carbon mol % selectivity to propylene. By using catalyst recycle to cool the average temperature of the catalyst entering the reactor, the same amount of heat can be added at a lower temperature which allows catalytic activity to be maintained while minimizing the thermal reaction of propane. The result of this is an overall higher propylene selectivity.

Embodiments of the disclosed process further permit the combined regenerated and recycle catalyst stream to maintain an acceptable propylene yield (equal to or greater than 30%) for dehydrogenation of the propane. All individual values and subranges from equal to or greater than 30% propylene yield are included and disclosed herein; for example, the combined regenerated catalyst and recycle catalyst stream may exhibit a propylene yield of at least 30, 35, 40, 42, 44, 48, 52, or 55%. In specific embodiments, the propylene yield is from 30 to 40%, or in the alternative, from 30 to 55%, or in the alternative, from 40 to 55%, or in the alternative, from 35 to 50%.

Dehydrogenation Catalysts

Preferred catalysts for use in the present invention are very active and are capable of dehydrogenating the selected hydrocarbon feed usually in less than 10 seconds at dehydrogenation reaction temperatures. Catalyst selection to meet the reaction time preferences is therefore important to ensuring that the benefits of the short contact time, including driving the equilibrium reaction to increase conversion, improving the selectivity, reducing by-product formation and product degradation, and ensuring and supporting appropriate catalyst regeneration, can be achieved. These preferred catalysts include solid particulate types which are capable of fluidization and, preferably, those which exhibit properties known in the industry as "Geldart A" properties. In addition Geldart B catalyst may also be used, though such may be, in some embodiments, less preferred. These catalysts are classified as "Group A" or "Group B" according to D. Geldart, *Gas Fluidization Technology*, John Wiley & Sons (New York, 1986), 34-37; and D. Geldart, "Types of Gas Fluidization," *Powder Technol.* 7 (1973) 285-292, which are incorporated herein by reference in their entireties. Those skilled in the art will be familiar with the categorization of particles based upon their mean particle size ($\bar{d}_p$) and particle density ($\rho_p$) under ambient conditions, which determines their fluidization behavior in a given carrier, but for further understanding herein, FIG. 1, generally termed a simplified "Geldart fluidization diagram," as published in 1973 in D. Geldart, "Types of Gas Fluidization," cited supra, is provided. The four Geldart "Group" classifications, A-D, are shown in FIG. 1, with the groups applicable to the inventive process, Groups A and B, generally termed as "aeratable" and "sand-like," respectively.

Group A is understood by those skilled in the art as representing an aeratable powder, having a bubble-free range of fluidization; a high bed expansion; a slow and linear deaeration rate; bubble properties that include a predominance of splitting/recoalescing bubbles, with a maximum bubble size and large wake; high levels of solids mixing and gas backmixing, assuming equal U-$U_{mf}$ (U is the velocity of the carrier gas, and $U_{mf}$ is the minimum fluidization velocity, typically though not necessarily measured in meters per second, m/s, i.e., there is excess gas velocity); axisymmetric slug properties; and no spouting, except in very shallow beds. The properties listed tend to improve as the mean particle size decreases, assuming equal $d_p$); or as the <45 micrometers (μm) proportion is increased; or as pressure, temperature, viscosity, and density of the gas increase. In general, the particles exhibit a small mean particle size and/or low particle density (<1.4 grams per cubic centimeter, g/cm³), fluidize easily, with smooth fluidization at low gas velocities, and exhibit controlled bubbling with small bubbles at higher gas velocities.

Group B is understood by those skilled in the art as representing a "sand-like" powder that starts bubbling at $U_{mf}$; that exhibits moderate bed expansion; a fast deaeration; no limits on bubble size; moderate levels of solids mixing and gas backmixing, assuming equal U-$U_{mf}$; both axisymmetric and asymmetric slugs; and spouting in only shallow beds. These properties tend to improve as mean particle size decreases, but particle size distribution and, with some uncertainty, pressure, temperature, viscosity, or density of gas seem to do little to improve them. In general, most of the particles having a particle size ($\bar{d}_p$) of 40 μm<$\bar{d}_p$<500 μm when the density ($\rho_p$) is 1.4<$\rho_p$<4 g/cm³, and preferably 60 μm<$\bar{d}_p$<500 μm when the density ($\rho_p$) is 4 g/cm³ and 250 μm<$\bar{d}_p$<100 μm when the density ($\rho_p$) is 1 g/cm³. These particles fluidize well with vigorous bubbling action and bubbles that grow large.

It is noted that a variety of closely-related but alternative definitions of the Geldart Groups are provided in additional literature articles, and that powder technology is considered to be an active field of research, but the above definitions are generally applicable to the present invention and the scope thereof.

Suitable examples of the defined catalysts include gallium-based catalysts such as those described in U.S. Pat. No. 6,031,143 and WO2002/096844, the disclosures of which are incorporated herein by reference in their entireties. One such catalyst that may be prepared such that it meets the Geldart A or Geldart B definition comprises gallium and platinum supported on alumina in the delta or theta phase, or in a mixture of delta plus theta phases, or theta plus alpha phases, or delta plus theta plus alpha phases, modified with silica, and having a surface area preferably less than about 100 square meters per gram (m²/g), as determined by the BET method. In preferred embodiments, the catalyst comprises:

i) from 0.1 to 34 wt %, preferably 0.2 to 3.8 wt %, gallium oxide ($Ga_2O_3$);
ii) from 1 to 300 parts per million (ppm), preferably 50 to 300 ppm, by weight platinum;
iii) from 0 to 5 wt %, preferably 0.01 to 1 wt %, of an alkaline and/or earth-alkaline such as potassium;
iv) from 0.08 to 3 wt % silica;
v) the balance to 100 wt % being alumina.

Similar gallium-based catalysts, further comprising manganese, are described in greater detail in WO 2003/053567; U.S. Patent Publication 2004/02242945, which further includes zinc; and EP 0637578 (B1). The descriptions of the catalysts in these documents are expressly incorporated herein in their entireties by reference.

Another suitable catalyst for the dehydrogenation reaction is based on chromium and comprises:

i) from 6 to 30 weight percent (wt %), preferably, from 13 to 25 wt %, of chromium oxide ($Cr_2O_3$);
ii) from 0.1 to 3.5 wt %, most preferably, from 0.2 to 2.8 wt %, stannous oxide (SnO);
iii) from 0.4 to 3 wt %, most preferably, from 0.5 to 2.5 wt %, of an alkaline oxide, for example, potassium oxide;
iv) from 0.08 to 3 wt % silica;
v) the balance to 100 wt % being alumina in the delta or theta phase, or a mixture of delta plus theta phases, or theta plus alpha phases, or delta plus theta plus alpha phases.

The catalysts described hereinabove can be used as-is or in combination with one or more additional materials, such as an inert material, for example, alpha-alumina, and/or modified with oxides of alkaline metals and/or silica, at a concentration of the inert material of from 0 to 50 wt %.

Those skilled in the art will be familiar with the above catalyst types and how to prepare or commercially obtain them without further instruction. However, additional details on the preparation of the aforementioned catalysts and their more preferred species may be found in, for example, U.S. Pat. No. 6,031,143 and EP 0637578 (B1), the disclosures of which are incorporated herein by reference in their entireties. Typically, the process of preparing the aforementioned dehydrogenation catalysts comprises dispersing precursors of the catalyst metals, for example, solutions of soluble salts of the selected catalyst metals, onto a carrier comprising alumina, silica, or a combination thereof. An example of an applicable dispersion process may comprise impregnating the carrier with one or more solutions containing the precursors of the selected catalyst metals, for example, gallium and platinum, chromium and tin, or the like, followed by drying and calcinations of the impregnated carrier. An alternative method may comprise ion adsorption of the catalyst metals, followed by separation of the liquid portion of the adsorption solution; drying; and activating the resultant solid.

EXAMPLES

The following examples illustrate the present invention but are not intended to limit the scope of the invention.

Several examples of the use of a used dehydrogenation catalyst subjected to a reactor recycle catalyst fluidization zone for varying time and under varying temperatures were tested for propane conversion activity and propylene selectivity. The catalyst used in the examples the catalyst comprises:

i) from 0.1 to 34 wt %, preferably 0.2 to 3.8 wt %, gallium oxide ($Ga_2O_3$);

ii) from 1 to 300 parts per million (ppm), preferably 50 to 300 ppm, by weight platinum;

iii) from 0 to 5 wt %, preferably 0.01 to 1 wt %, of an alkaline and/or earth-alkaline such as potassium;

iv) from 0.08 to 3 wt % silica;

v) the balance to 100 wt % being alumina.

All of the inventive examples ("Inv #") were soaked in a fluidization gas containing 60 vol % methane and 40 vol % Nitrogen. Comparative Example 1 ("Comp. 1") utilized the catalyst as described above with a fluidization gas of 100% nitrogen. Table 1 provides the results of such testing. These tests were conducted in a fixed bed lab reactor. During the experiment, the catalyst was heated slowly to reaction temperature with an inert, then the catalyst was treated with air at 750° C. for 15 minutes, the catalyst was cooled with nitrogen to the target temperature, then methane was feed for the required time, nitrogen cooled the catalyst to reaction temperature, then propane was feed at a Weight Hourly Space Velocity (WHSV) of 10 at 625° C. and the composition of the product was measured after 30 seconds on stream. As can be seen in Table 1, exposure to methane at the expected reactor recycle fluidization section conditions (620° C. for 120 seconds) does not deactivate the catalyst as is seen when catalyst is exposed to steam. Secondarily, exposure to methane at the expected catalyst mixing conditions (640-680° C. for 120 seconds) does not significantly deactivate the regenerated and recycled catalyst.

TABLE 1

| Example | Temperature ° C. | Time in Reactor recycle catalyst fluidization Zone or Catalyst Mixing Zone with methane contacting seconds | % Propane Conversion | % Propylene Yield |
| --- | --- | --- | --- | --- |
| Comp. 1 | 625 | 0 | 44.09 | 41.91 |
| Inv. 1 | 625 | 120 | 43.06 | 40.88 |
| Inv. 2 | 650 | 120 | 42.15 | 40.01 |
| Inv. 3 | 650 | 30 | 43.86 | 41.65 |
| Inv. 4 | 680 | 120 | 36.61 | 34.49 |
| Inv. 5 | 750 | 30 | 43.85 | 41.64 |
| Inv. 6 | 750 | 120 | 34.93 | 32.72 |

Test Methods

Test methods include the following: The conversion and selectivity of the crude propylene product was calculated based on the measured composition from a gas chromatograph after the catalyst had been exposed to propane at operating temperature for 30 seconds.

The present invention may be embodied in other forms without departing from the spirit and the essential attributes thereof, and, accordingly, reference should be made to the appended claims, rather than to the foregoing specification, as indicating the scope of the invention.

The invention claimed is:

1. A process for catalytic dehydrogenation comprising:
catalytically dehydrogenating a hydrocarbon feed in the presence of a dehydrogenation catalyst in a fluidized bed catalytic dehydrogenation reactor to produce a product stream comprising used catalyst and at least one dehydrogenated hydrocarbon;
separating the used catalyst from gaseous components of the product stream;
mixing a fluidization gas which comprises at least 60 vol. % methane with at least a portion of the used catalyst in a catalyst fluidization section to fluidize the at least a portion of the used catalyst to produce at least a catalyst recycle stream; and
recycling the catalyst recycle stream either directly or indirectly into the fluidized bed catalytic dehydrogenation reactor.

2. The process for catalytic dehydrogenation according to claim 1, further comprising:
passing the catalyst recycle stream to a mixing zone wherein the catalyst recycle stream is mixed with a regenerated catalyst to form a mixed catalyst stream, wherein said mixing occurs at a temperature of from 500 to 800° C. for a period of from 1 second to 3 minutes, as measured with a thermocouple within the mixing zone; and
subsequently feeding the mixed catalyst stream to the fluidized bed catalytic dehydrogenation reactor.

3. The process for catalytic dehydrogenation of propane according to claim 2, wherein said mixing occurs at a temperature of from 640 to 680° C., as measured with a thermocouple at an outlet of the mixing zone.

4. The process for catalytic dehydrogenation according to claim 1, wherein the mixing the fluidization gas with the at least a portion of the used catalyst occurs in the catalyst fluidization section at a temperature of from 500 to 800° C. for a period of from 1 second to 3 minutes, as measured with a thermocouple within the stripping section.

5. The process for catalytic dehydrogenation according to claim 1, wherein the hydrocarbon feed comprises propane and the at least one dehydrogenated hydrocarbon comprises propene.

6. The process for catalytic dehydrogenation according to claim 5, wherein the propane conversion to propylene in the fluidized bed catalytic dehydrogenation reactor is from 30 to 55 wt %.

7. The process for catalytic dehydrogenation according to claim 1, wherein the recycle catalyst stream has greater than 80% of the dehydrogenation activity of the used catalyst exiting the catalyst separation zone.

8. The process for catalytic dehydrogenation according to claim 1, further comprising injecting a hydrocarbon feed into the fluidized bed catalytic dehydrogenation reactor.

9. The process for catalytic dehydrogenation according to claim 8, wherein the hydrocarbon feed comprises one or more selected from the group consisting of ethane, propane, n-butane, isobutane, isobutene, ethylbenzene, propylbenzene and methylethylbenzene.

10. The process for catalytic dehydrogenation according to claim 1, comprising mixing the used catalyst with a gaseous stream comprising at least 40 vol. % fluidization gas in the catalyst fluidization section to produce the catalyst recycle stream.

11. The process for catalytic dehydrogenation according to claim 1, wherein the catalyst fluidization section comprises a stripping section and mixing the fluidization gas with the at least a portion of the used catalyst strips the used catalyst.

12. The process for catalytic dehydrogenation according to claim 11, further comprising passing at least a portion of the stripped used catalyst to a catalyst regeneration process.

13. The process for catalytic dehydrogenation according to claim 1, wherein a catalyst separation step in the catalyst separation zone terminates in a stripping section and a catalyst fluidization section separate from the stripping section and the process further comprises:
    passing a portion of used catalyst entering the stripping section to a catalyst regeneration process; and
    passing the portion of a used catalyst stream from the catalyst fluidization section directly to the fluidized bed catalytic dehydrogenation reactor or to a mixing zone prior to being passed to the fluidized bed catalytic dehydrogenation reactor.

14. A process for catalytic dehydrogenation comprising:
    catalytically dehydrogenating a hydrocarbon feed in the presence of a dehydrogenation catalyst in a fluidized bed catalytic dehydrogenation reactor to produce a product stream comprising used catalyst and at least one dehydrogenated hydrocarbon;
    separating the used catalyst from gaseous components of the product stream;
    passing used catalyst to a reactor recycle catalyst fluidization section and to a stripping section separate from the catalyst fluidization section;
    in the catalyst fluidization section, mixing a fluidization gas comprising methane, natural gas, ethane, hydrogen, nitrogen, or any combination thereof with the used catalyst stream passed to the catalyst fluidization section to form a catalyst recycle stream;
    in the stripping section, contacting a stripping gas with the used catalyst passed to the stripping section to produce a stripped used catalyst;
    recycling the catalyst recycle stream either directly or indirectly into the fluidized bed catalytic dehydrogenation reactor; and
    passing at least a portion of the stripped used catalyst to a catalyst regeneration process.

15. The process for catalytic dehydrogenation of claim 14, comprising recycling the catalyst recycle stream directly to the fluidized bed catalytic dehydrogenation reactor.

16. The process for catalytic dehydrogenation of claim 14, comprising recycling the catalyst recycle stream to a mixing zone upstream of the catalytic dehydrogenation reactor.

17. The process for catalytic dehydrogenation according to claim 14, wherein the fluidization gas comprises 60 vol. % methane.

18. The process for catalytic dehydrogenation according to claim 14, comprising mixing the fluidized catalyst stream with a gaseous stream comprising at least 40 vol. % fluidization gas in the catalyst fluidization section.

* * * * *